US008202970B1

(12) United States Patent
Nghiem et al.

(10) Patent No.: US 8,202,970 B1
(45) Date of Patent: Jun. 19, 2012

(54) METHOD FOR IMPROVING THE BIOAVAILABILITY OF POLYSACCHARIDES IN LIGNOCELLULOSIC MATERIALS

(75) Inventors: Nhuan P. Nghiem, Lansdale, PA (US); Tae H. Kim, Ames, IA (US); Kevin B. Hicks, Malvern, PA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 873 days.

(21) Appl. No.: 12/194,821

(22) Filed: Aug. 20, 2008

(51) Int. Cl.
*C07G 1/00* (2011.01)
*C08H 7/00* (2011.01)
*C08L 97/00* (2006.01)
*C12P 7/06* (2006.01)
*C12P 7/08* (2006.01)
*C12P 7/10* (2006.01)

(52) U.S. Cl. ......... 530/507; 435/161; 435/163; 435/165
(58) Field of Classification Search .................. 530/507; 435/161, 163, 165
See application file for complete search history.

(56) References Cited

U.S. PATENT DOCUMENTS 6,147,206 A 11/2000 Doner et al.

OTHER PUBLICATIONS

Mark T. Holtzapple "The Effect of Organosolv Pretreatment on the Enzymatic Hydrolysis of Poplar" Biotechnology and Bioengineering, vol. XXVI, pp. 670-676 (1984).*
U.S. Dept. of Energy & U.S. Dept. of Agriculture, "Biomass as Feedstock for a Bioenergy and Bioproducts Industry: The Technical Feasibility of a Billion-Ton Annual Supply", Apr. 2005.
U.S. Dept. of Energy, "Breaking the Biological Barriers to Cellulosic Ethanol: A Joint Research Agenda", DOE/SC-0095, U.S. Department of Energy Office of Science and Office of Energy and Renewabele Energy, 2006.
Anderson, E. et al., "Hemicelluloses from Cottonseed Hulls", J. of Biological Chemistry, vol. 126, (1), 1938, pp. 175-179.
Dunlap, C.E. et al., "Treatment Process to Increase Cellulose Microbial Digestibility", Biochemical Engineering-Energy, Renewable Resources and New Foods, vol. 72, (158), 1976, pp. 58-63.
Brown, L. et al., "Enzymatic Saccharification of Lignocellulosic Biomass" Chemical Analysis and Testing Task Laboratory Analytical Procedure, NREL Ethanol Project, LAP-009, Aug. 26, 1996, pp. 1-8.
Chang, V.S. et al.. "Fundamental Factors Affecting Biomass Enzymatic Reactivity", Applied Biochemistry and Biotechnology, vol. 84-86, 2000, pp. 5-37.
Collins, K, "The New World of Biofuels: Implications for Agriculture and Energy", EIA Energy Outlook, Modeling, and Data Conference, Mar. 28, 2007.
Cowlings. E.B. et al., "Properties of Cellulose and Lignocellulosic Materials as Substrates for Enzymatic Conversion Process", Biotechnology and Bioengineering Symposium, No. 6, 1976, pp. 95-123.

Gaspar, M. et al.. "Corn Fiber as a Raw Material for Hemicellulose and Ethanol Production", Process Biochemistry, vol. 42, 2007. pp. 1135-1139.
Gaspar, M. et al.. "Fractionation and Utilisation of Corn Fibre Carbohydrates", Process Biochemistry, vol. 40, 2005, pp. 1183-1188.
Hess, K. et al., "Cellulosic Biomass Feedstocks and Logistics for ETOH", US. Department of Energy: GEC Meeting, Feb. 27-28, 2007.
Kim, T.H. et al., "Pretreatment and Fractionation of Corn Stover by Soaking in Ethanol and Aqueous Ammonia", Appl. Biochem. Biotechnol., DOI 10.1007/s12010-009-8524-0, 2009.
Kim, S. et al., "Global Potential Bioethanol Production from Wasted Crops and Crop Residue", Biomass and Bioenergy, vol. 26, 2004, pp. 361-375.
Kim, T.H. et al., "Pretreatment of Corn Stover by Soaking in Aqueous Ammonia at Moderate Temperatures", Applied Biochemistry and Biotechnology, vol. 136-140, 2007, pp. 81-92.
Kim, T.H. et al., "Pretreatment of Corn Stover by Soaking in Aqueous Ammonia", Applied Biochemistry and Biotechnology, vol. 121-124; 2005, pp. 1119-1132.
Kim. T.H. et al., "Pretreatment of Corn Stover by Aqueous Ammonia", Bioresource Technology, vol. 90, 2003, pp. 39-47.
Converse, A.O., "Substrate Factors Limiting Enzymatic Hydrolysis", Bioconversions of Forest and Agricultural Plant Residues, Biotechnology in Agriculture Series. 1993, pp. 93-106.
Selig, M. et al., "Enzymatic Saccharification of Lignocellulosic Biomass", Technical Report NREL/TP-510-42629, Mar. 2008, pp. 1-5.
Shatalov, A.A. et al., "Ethanol-Enhanced Alkaline Pulping of Arundo donax L. Reed: Influence of Solvent on Pulp Yield and Quality", Holzforschung, vol. 56, (5), 2002, pp. 507-512.
Sluiter, A. et al., "Procedure Title: Determination of Structural Carbohydrates and Lignin in Biomass", Biomass Analysis Technology Team Laboratory Analytical Procedure, NREL Biomass Program, Version 2006. Jul. 17, 2005.
Sluiter, A. et al., "Procedure Title: Determination of Structural Carbohydrates and Lignin in Biomass", Laboratory Analytical Procedure, NREL, Technical Report NREL/TP-510-42618, Apr. 25, 2008.
Sun, RC et al., "Fractional Separation and Physico-Chemical Analysis of Lignins from the Black Liquor of Oil Palm Trunk Fibre Pulping", Separation and Purification Technology, vol. 24, 2001. pp. 529-539.
Sun, R.C. et al., "Fractional isolation, Physico-Chemical Characterization and Homogeneous Esterification of Hemicelluloses form Fast-Growing Poplar Wood", Carbohydrate Polymers, vol. 44, 2001, pp. 29-39. Sun, X.F. et al., "Isolation and Characterisation of Cellulose Obtained by a Two-Stage Treatment with Organosolv an Cyanamide Activated Hydrogen Peroxide from Wheat Straw", Carbohydrate Polymers, vol. 55, 2004, pp. 379-391.
Whistler, R.L. et al., "Hemicelluloses", The Carbohydrates, Chemistry and Biochemistry, vol. IIA, 2nd Edition. 1970, pp. 447-469.

* cited by examiner

*Primary Examiner* — Sandra Saucier
*Assistant Examiner* — Thane Underdahl
(74) *Attorney, Agent, or Firm* — John D. Fado; G. Byron Stover

(57) ABSTRACT

A method for improving the bioavailability of polysaccharides in lignocellulosic materials, involving reacting lignocellulosic materials with ammonia and ethanol.

24 Claims, 6 Drawing Sheets

US 8,202,970 B1

METHOD FOR IMPROVING THE BIOAVAILABILITY OF POLYSACCHARIDES IN LIGNOCELLULOSIC MATERIALS

BACKGROUND OF THE INVENTION

The present invention relates to a method for improving the bioavailability of polysaccharides in lignocellulosic materials, involving reacting lignocellulosic materials with ammonia and ethanol.

Interest in renewable liquid fuels such as ethanol is increasing worldwide. In the United States, the goal is to produce 60 billion gallons of ethanol per year to replace 30% of the nation's gasoline consumption by 2030 (U.S. Department of Energy, Breaking the Biological Barriers to Cellulosic Ethanol: A Joint Research Agenda, Report No. DOE/SC-0095 (2006)). Currently most of the fuel ethanol produced commercially in the U.S. is made from corn. Corn ethanol alone is not sufficient to meet the stated goal since the maximum production has been estimated to be only about 12 to 15 billion gallons per year (Collins, K., The New World of Biofuels: Implications for Agriculture and Energy, EIA Energy Outlook, Modeling, and Data Conference, Mar. 28, 2007, Washington, D.C.; Hess, R., et al., Cellulosic Biomass Feedstocks and Logistics for ETOH, GEC Meeting, Feb. 27-28, 2007, Washington, D.C.). Thus, a renewable feedstock for ethanol production other than corn is needed, and considerable attention has been given to lignocellulosic biomass. The three main sources of lignocellulosic biomass are forest products and residues, agricultural residues, and dedicated energy crops. Corn stover contributes the largest quantities among the agricultural residues in the U.S. Currently 75 million metric tons (MT) of corn stover can be sustainably collected and used for ethanol production. It has been estimated that by the mid-21st century, 232 million dry metric tons of corn stover would be available for ethanol production (Perlack, R. D., et al., Biomass Feedstock for a Bioenergy and Bioproducts Industry The Technical Feasibility of a Billion-ton Annual Supply, U.S. Department of Energy and U.S. Department of Agriculture (2005)). The potential ethanol yield of corn stover has been estimated to be 0.29 liter per kg (76.61 gallons per MT) (Kim, S., and B. E. Dale, Biomass and Bioenergy, 26: 361-375 (2004)). Thus, by the mid-21st century, 18 billion gallons of ethanol can be produced from corn stover alone.

Lignocellulosic feedstocks consist of three main components: cellulose, hemicellulose, and lignin. Bioconversion of these feedstocks via the sugar route requires enzymatic hydrolysis of cellulose and hemicellulose to fermentable sugars, which subsequently are fermented to ethanol. Normally a pretreatment process is needed for efficient hydrolysis of the two carbohydrate fractions by enzymes. Typically in a pretreatment process some of the lignin is removed to increase accessibility of cellulose and hemicellulose to enzymes (U.S. Department of Energy, Breaking the Biological Barriers to Cellulosic Ethanol: A Joint Research Agenda, Report No. DOE/SC-0095 (2006)). Since the objective of lignocellulosic biomass conversion is to produce ethanol from the fermentable sugars derived from cellulose and hemicellulose, it is obvious that a good pretreatment process should preserve as much of these two carbohydrate fractions as possible.

Soaking in aqueous ammonia (SAA) has been proven to be an effective pretreatment method for lignocellulosic biomass (Kim, T. H., and Y. Y. Lee, Appl. Biochem. Biotechnol., 137-140: 81-92 (2007); Kim, T. H., and Y. Y. Lee, Appl. Biochem. Biotechnol., 124: 1119-1132 (2005)). SAA is one of the few methods for pretreatment of lignocellulosic biomass in which almost 100% glucan and about 80% xylan are retained whereas a significant percentage of lignin is removed. Despite this high efficiency in carbohydrate preservation about 20% xylan is solubilized together with lignin and hence is not available for conversion to ethanol in the subsequent fermentation step.

Thus there is a need to reduce the loss of xylan due to solubilization.

SUMMARY OF THE INVENTION

In accordance with the present invention there is provided a method for improving the bioavailability of polysaccharides in lignocellulosic materials, involving reacting lignocellulosic materials with ammonia and ethanol.

DETAILED DESCRIPTION OF THE INVENTION

Figure 1:
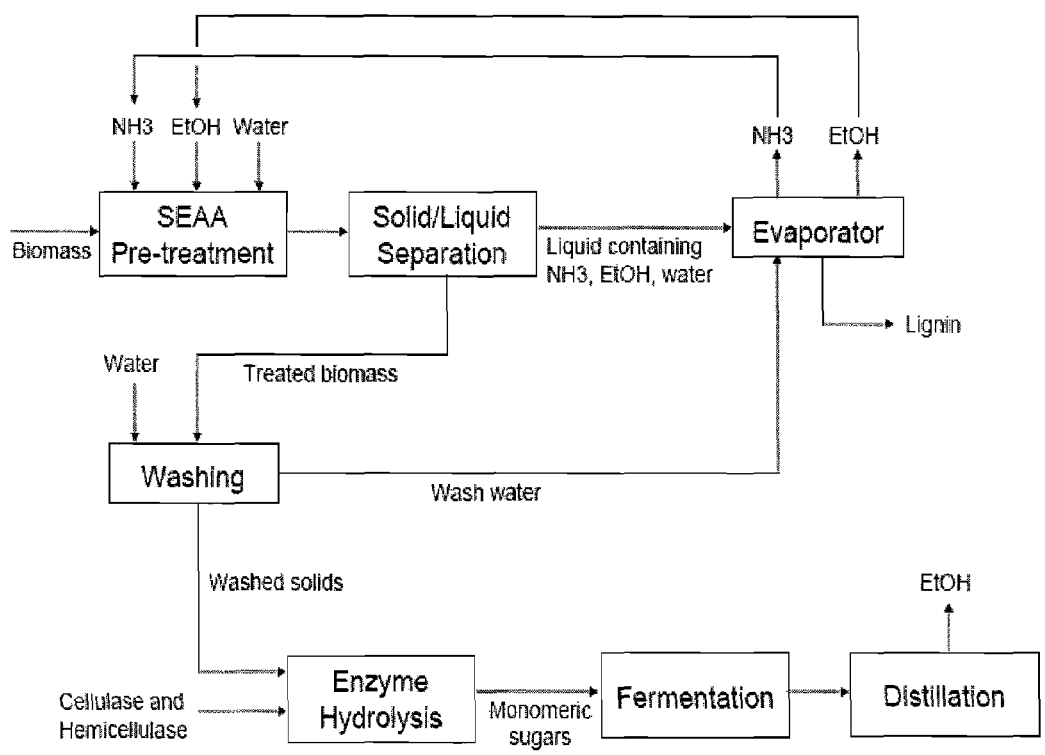
FIG. 1 shows bioconversion of corn stover using the proposed SEAA (Soaking in Ethanol and Aqueous Ammonia) process.

We have developed a method which we call the Soaking in Ethanol and Aqueous Ammonia (SEAA) method. The schematic diagram of the SEAA method is shown in FIG. 1. The new method reduced the loss of xylan due to partial solubilization of xylan when lignocellulosic biomass (e.g., corn stover) was treated with aqueous ammonia. In the SEAA method ethanol was added to aqueous ammonia solution. Without being bound by theory, the presence of ethanol in the aqueous ammonia caused re-precipitation of the previously solubilized xylan onto the solid matrix or reduced the extent of hemicellulose solubilization. Thus, more xylan (generally more than about 83% (e.g., more than 83%), preferably more than about 90% (e.g., more than 90%), more preferably about 94% (e.g., 94%), most preferably more than about 94% (e.g., more than 94%)) was available for conversion to products such as ethanol. The ethanol used in the treatment of lignocellulosic biomass was recovered and recycled.

The lignocellulosic biomass was soaked with an ammonia-ethanol solution and heated, either simultaneously or consecutively. Generally both soaking and heating happen in the same reactor at the same time, and the heating time from the ambient temperature to the desired temperature is included in the total reaction time. Generally the total reaction time (soaking and heating) is about 1 hour to about 72 hours (e.g., 1-72 h; preferably about 8 hours to about 48 hours (e.g., 8-48 h), more preferably about 12 hours to about 24 hours (e.g., 12-24 h), more preferably about 20 hours to about 24 hours (e.g., 20-24 h), most preferably about 24 hours (e.g., 24 h)). The mixture of lignocellulosic biomass and ammonia-ethanol solution is heated to about ambient to about 170° C. (e.g., ambient-170° C.; preferably about 40° C. to about 120° C. (e.g., 40°-120° C.)., more preferably about 50° C. to about 100° C. (e.g., 50°-100° C.)., more preferably about 50° C. to about 70° C. (e.g., 50°-70° C.)., most preferably about 60° C. (e.g., 60° C.)). Generally, the ammonia loading was kept constant at about 1 to about 30 wt % (e.g., 1-30 wt %; preferably about 5 wt % to about 25 wt % (e.g., 5-25 wt %), more preferably about 10 wt % to about 20 wt % (e.g., 10-20 wt %), more preferably about 14 wt % to about 16 wt % (e.g., 14-16 wt %), most preferably about 15 wt % (e.g., 15 wt %)) of the total liquid and the solid:liquid ratio was maintained at about 1:2 to about 1:15 (e.g., 1:2-1:15; preferably about 1:4 to about 1:12 (e.g., 1:4-1:12), more preferably about 1:6 to about 1:10 (e.g., 1:6-1:10 h), most preferably about 1:9 (e.g., 1:9)). The amount of ethanol can be from about 1 wt % to about 49 wt % (e.g., 1-49 wt %; preferably about 5 wt % to about 35 wt % (e.g., 5-35 wt %), more preferably about 10 wt % to about 25 wt % (e.g., 10-25 wt %), more preferably about 18 wt % to about 22 wt % (e.g., 18-22 wt %), most preferably about 20 wt % (e.g., 20 wt %)). Ethanol at 49 wt % is the maximum concentration which can be applied since 30 wt % is the maximum concentration of commercially available ammonium hydroxide solutions. When the reaction was completed, the solids (treated biomass) and liquids were separated by methods known in the art. Ethanol and ammonia were separated from the liquids by methods known in the art. The solids were washed to get rid of the residual lignin-containing liquid, and then hydrolyzed with enzymes (e.g., cellulase, hemicellulase) to produce fermentable sugars for subsequent bioconversion to ethanol or other industrial chemicals of interest.

As used throughout the specification, "bioavailability" refers to the relative ability of a particular material to be hydrolyzed by cellulase and related enzymes, or, in the alternative, to the relative utility of a particular material as a carbohydrate source in microbial fermentation. Thus, materials with increased bioavailability, as that term is employed herein, are more readily hydrolyzed by cellulases, or more readily degraded and metabolized by microbial activity. "Polysaccharide," as employed throughout the specification, refers to polymeric constituents of lignocellulosic materials which comprise repeating monosaccharide units. Exemplary polysaccharides include cellulose in the various forms found in lignocellulosic materials, and hemicelluloses such as xylans, arabinans, mannans, and galactans. As used herein, "lignocellulosic materials" refers generally to plant tissue, particularly structural plant tissue comprising complex associations of polysaccharides and lignin. Exemplary materials within this definition include agricultural waste materials (e.g., corn stover) and by-products, hardwoods and softwoods.

Suitable agricultural waste materials and by-products to be treated by the method of the present invention can be derived from any source. Examples of such materials include cornstalks, corn cobs, wheat, oat, and barley straw, and bagasse. These materials are generally considered poor fodder for animals or poor substrates for rapid microbial fermentation, due to the relative indigestibility of cellulose and related polysaccharides, which are the principal components of these materials. However, following treatment by the method of the present invention, approximately more than 90 percent of the available polysaccharides in the form of cellulose and hemicelluloses can be converted to monosaccharides by cellulases.

Generally, the method of the present invention is conducted within a closed reaction system arranged to enable recovery of ammonia and ethanol upon evaporation at the conclusion of treatment.

The critical variables to be monitored in treating lignocellulosic materials include temperature, pressure, amount of ethanol, and ammonia density. Each of these parameters must be maintained within prescribed limits to attain supercritical or near-supercritical states for fluid ammonia, with the attendant advantages in treatment efficacy. Thus, process temperatures should be maintained between about ambient –170° C., preferably between 40°-120° C., more preferably about 50°-100° C., most preferably about 60° C. For best results, this temperature should be maintained from about 1 hour to 72 hours (e.g., 1-72 h; preferably about 8 hours to about 48 hours (e.g., 8-48 h), more preferably about 12 hours to about 24 hours (e.g., 12-24 h), most preferably about 24 hours (e.g., 24 h)).

Process pressures are generally maintained at higher pressure than the vapor pressure of pretreatment reagent mixture (aqueous ammonia+ethanol) to ensure the liquid phase reaction. Ammonia loadings are maintained from 1 to 30 wt % (e.g., 1-30 wt %; preferably about 5 wt % to about 25 wt % (e.g., 5-25 wt %), more preferably about 10 wt % to about 20 wt % (e.g., 10-20 wt %), most preferably about 15 wt (e.g., 15 wt %)). The amount of ethanol can be from about 1 wt % to about 49 wt % (e.g., 1-49; preferably about 5 wt % to about 35 wt % (e.g., 5-35 wt %), more preferably about 10 wt % to about 25 wt % (e.g., 10-20 wt %), most preferably about 20 wt (e.g., 20 wt %)).

Following treatment in accordance with the method of the present invention, the resulting products can be further processed by enzymatic hydrolysis to provide mixtures of monosaccharides suitable for fermentation to ethanol by yeast or other suitable ethanologenic microorganisms, or used directly as carbohydrate sources in a variety of fermentation or bioconversion processes involving other organisms. Alternatively, the products of the method of the present invention can be used directly as substrates in fermentation processes.

Modest residues of ammonia are not harmful in subsequent fermentation steps, and can provide a beneficial nitrogen source.

Preferred enzymes for hydrolysis are cellulases and hemicellulases. If the products of the present invention are employed directly in fermentation processes, yeasts, bacteria, and recombinant yeast and bacteria are useful.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Corn stover: Corn stover was obtained from the National Renewable Energy Laboratory (NREL) in Golden, Colo. It was ground and screened. The fractions having particle sizes between 10 mesh and 35 mesh (0.5 mm and 2.0 mm) were used in the experiments. The ground and screened corn stover was air dried and stored at ambient temperatures. At equilibrium the moisture content of ground corn stover was approximately 5% to 8%. The composition of the corn stover is shown in Table 1.

Enzymes: Cellulase enzyme was GC-220 (Genencor, a Division of Danisco). The activity of the enzyme was 45 FPU/mL (FPU: filter paper unit) and its protein content was 184 mg/mL. The β-glucosidase enzyme was Novozyme 188. This enzyme had an activity of 750 CBU/mL (CBU: cellobiose unit).

Figure 2:
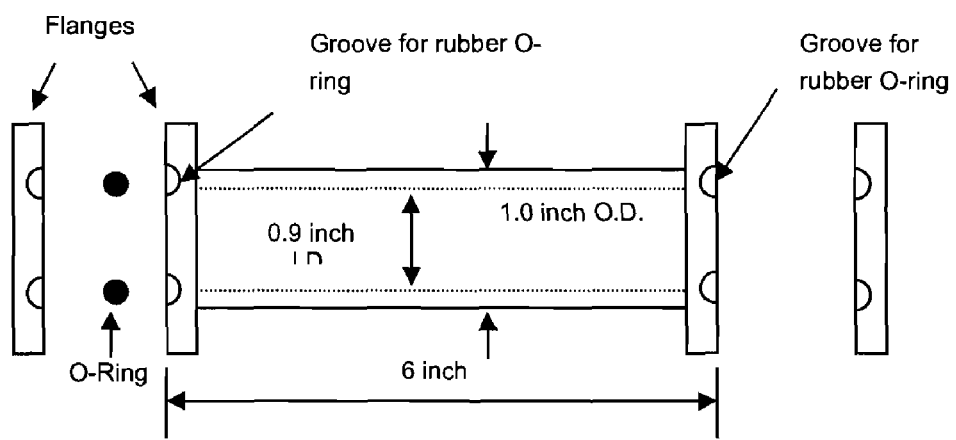
FIG. 2 shows the SEAA pretreatment reactor assembly used in the experiments described below.

Experimental Procedures: The pretreatment of corn stover was carried out in a reactor made of stainless steel 316 as shown in FIG. 2. In each experiment, 5 g corn stover (dry basis) was placed in the reactor and the ammonia-ethanol solution was added. The corn stover was allowed to soak in the ammonia-ethanol solution for a few minutes before the reactor was placed in a convection oven that was pre-set and subsequently maintained at 60° C. In all of the experiments, the ammonia loading was kept constant at 15 wt % of the total liquid and the solid:liquid ratio was maintained at 1:9, i.e., 5 g dry corn stover in 45 g total liquid. Four different ethanol levels were tested: 1, 5, 20, and 49 wt % of the total liquid (balance was water). Ethanol at 49 wt % was the maximum concentration which could be applied since 30 wt % was the maximum concentration of the commercially available ammonium hydroxide solution. An experiment in which no ethanol was added also was performed. The reaction time was 24 hours. At the end of the experiments the entire contents of the reactor were collected and filtered. The liquid was discarded and the solids were subject to compositional analysis and enzymatic digestibility tests.

The enzyme digestibility tests of the pretreated corn stover were performed in duplicate according to the National Renewable Energy Laboratory (NREL) Standard Method LAP-009 (LAP-009—Enzymatic Saccharification of Lignocellulosic (1996), National Renewable Energy Laboratory, Golden, Colo.). These tests were performed at 50° C. and pH 4.8 in 0.05 M sodium citrate buffer. Enzyme loading of 30 FPU of GC-220/g glucan supplemented with 30 CBU of β-glucosidase (Novozyme 188)/g glucan was used. The initial glucan concentration was 1% (w/v) based on 100 mL of total liquid and solid. All the samples used in the digestibility tests were wet samples as collected from various pretreatments. The 250 mL screw-capped Erlenmeyer flasks containing the enzyme hydrolysis preparations were placed in an incubator shaker (Lab-line, 4827F, Dubuque, Iowa) and agitated at 150 rpm. Samples were taken periodically (6, 12, 24, 48, 72 and 96 h) and analyzed for glucose, xylose, and cellobiose using High Performance Liquid Chromatography (HPLC). Total released glucose (or xylose) after 72 h of hydrolysis was used to calculate the enzymatic digestibility. Untreated corn stover was taken through the same procedure as a reference.

Analytical Methods: The solid samples, which included treated and untreated corn stover, were subject to compositional analysis according to the NREL standard method (Sluiter, A., et al., Determination of Structural Carbohydrates and Lignin in Biomass (2005), National Renewable Energy Laboratory, Golden, Colo.). Each sample was run in duplicate. Sugars were determined by HPLC. The system was an ISCO model 2350 (Lincoln, Nebr.) using de-ionized water as solvent at 0.6 mL/min combined with an Aminex® HPX-87P column (Bio-Rad Laboratories, Hercules, Calif.) operated at 85° C. and an HP 1047A refractive index (RI) detector (Hewlett Packard, Palo Alto, Calif.). The software used for data analysis was Chrom Perfect® Spirit version 4 build 17 (Justice Laboratory Software, Auchtermuchty, Fife, UK).

Results and Discussion. Retention of Hemicellulose by Ethanol Addition: The effects of ethanol at various concentrations on the compositions of the corn stover treated by the SEAA process are shown in Table 2. The results clearly indicate that the amounts of xylan remaining after the SEAA treatment surprisingly increased with increasing ethanol concentrations. The extents by which xylan was solubilized with no ethanol and with ethanol added at 1 wt %, 5 wt %, 20 wt %, and 49 wt % of the total liquid were calculated to be 17.2%, 16.7%, 14.5%, 10.4%, and 6.3% of the original xylan, respectively. Thus, at the highest ethanol concentration used the loss of hemicellulose in the liquid phase was reduced by 63%. Without being bound by theory, the decrease in the amounts of hemicellulose lost in the liquid phase demonstrated here was caused by re-precipitation of the hemicellulose that had previously been solubilized by addition of ethanol.

The results in Table 2 also show that glucan was well preserved even without ethanol addition. Preservation of the cellulose fraction of corn stover during pretreatment by soaking in liquid ammonia has been demonstrated (Kim, T. H., and Y. Y. Lee, Appl. Biochem. Biotechnol., 137-140: 81-92 (2007); Kim, T. H., and Y. Y. Lee, Appl. Biochem. Biotechnol., 124: 1119-1132 (2005)). Ethanol addition surprisingly also resulted in lower removal of lignin. However, the effect of ethanol on lowering the extent of delignification was small and not as significant as observed for hemicellulose retention.

Figure 3:
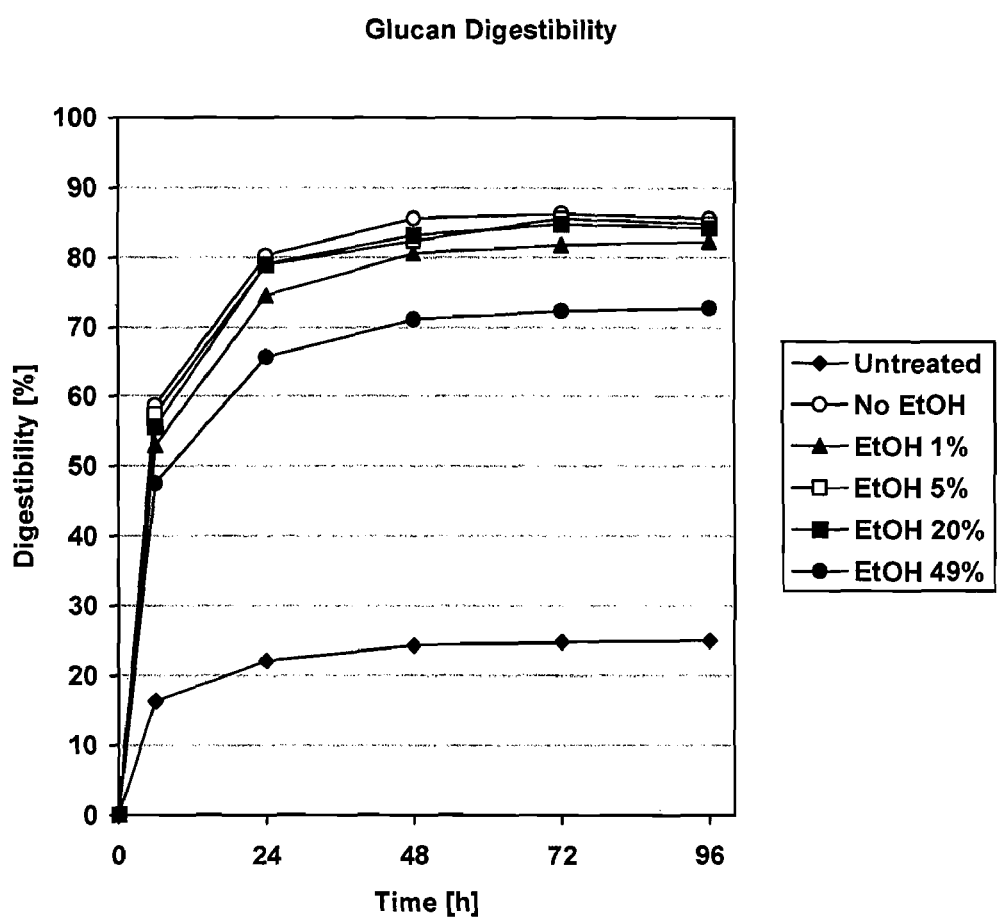
FIG. 3 shows the results of the enzyme digestibility tests of the SEAA-treated corn stover for glucan.
Figure 4:
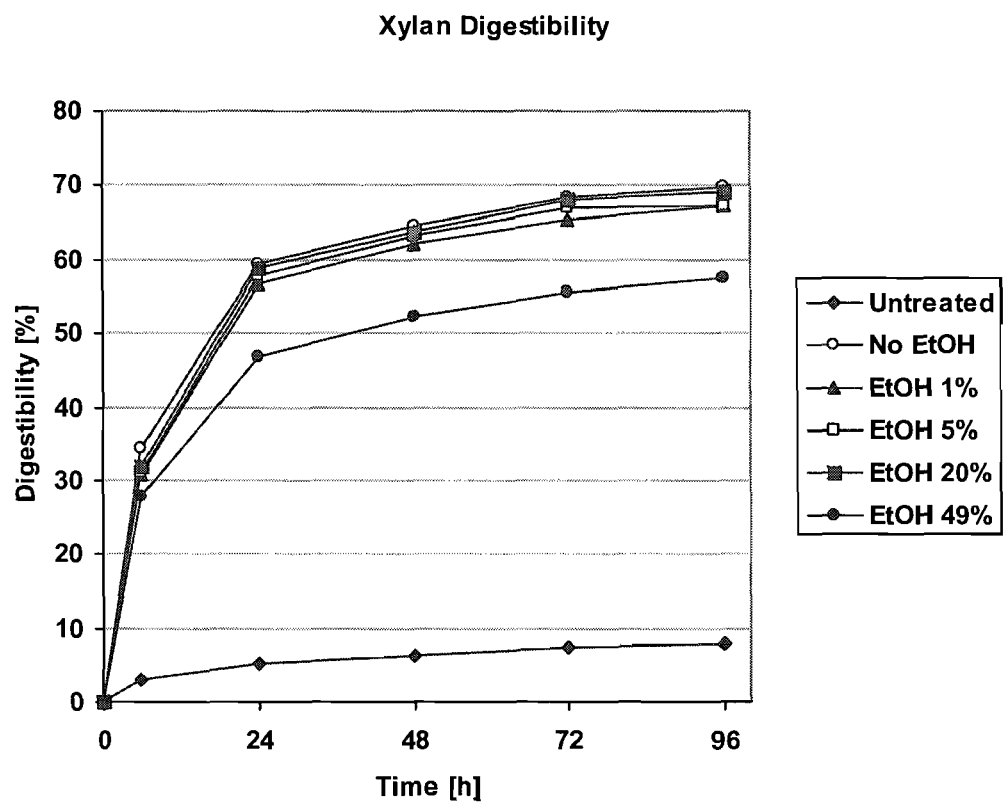
FIG. 4 shows the results of the enzyme digestibility tests of the SEAA-treated corn stover for xylan.
Figure 5:
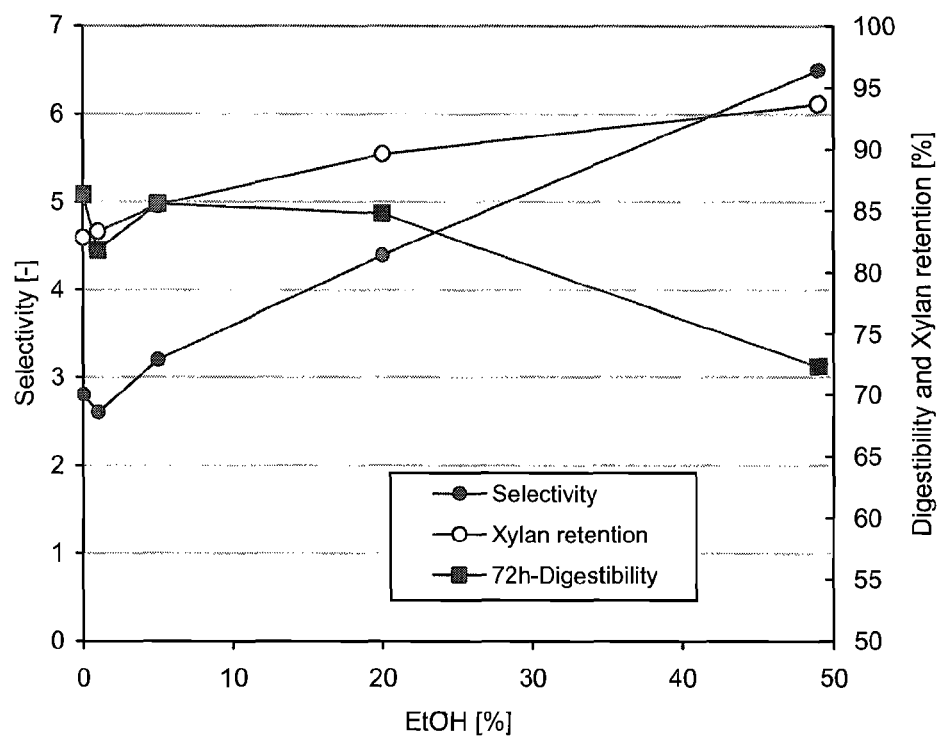
FIG. 5 shows selectivity of the SEAA-treated corn stover at various ethanol concentrations. Data in the figure are based on the oven-dried untreated biomass. Pretreatment conditions: 24 h of reaction time, 1:9 (weight basis) of solid:liquid ratio, 15 wt % ammonia concentration, 60° C. of reaction temperature. Selectivity=$m_{Lignin}/m_{Xylan}$ (where, $m_{Lignin}$ and $m_{Xylan}$ are the mass loss rate of lignin and xylan in the solid, respectively).

Enzyme Digestibility Test: The results of the enzyme digestibility tests of the SEAA-treated corn stover for glucan and xylan are shown in FIGS. 3 and 4 respectively. As described in the experimental procedure, the same amount of glucan (1% (w/v) based on total solid plus liquid) was used in each experiment. The results in Table 2 show that the glucan contents of the corn stover samples treated by the SEAA process using different ethanol concentrations were well preserved in each experiment, but other components (i.e., xylan and lignin) varied with ethanol concentrations. Thus, different amounts of treated corn stover were used in the enzyme digestibility experiments in order to maintain 1% (w/v) glucan loadings. Consequently, the initial amounts of xylan in each experiment were different. The digestibility was calculated based on the initial glucan and xylan loading in each experiment.

$$\text{Enzymatic Digestibilty (\%)} = \frac{\left(\begin{array}{c}\text{Monomeric sugar (glucose or xylose)}\\ \text{produced (g)} \times \text{hydration factor}\end{array}\right)}{\text{Initial glucan (1.0 g) or Xylan (g) in flasks}} \times 100$$

where, the hydration factor is 0.9 for glucose and 0.88 for xylose.

In all cases, the results plotted in FIGS. 3 and 4 surprisingly show considerably higher digestibility of both glucan and xylan respectively in the treated samples compared to the untreated sample. For both glucan and xylan the digestibility of the samples treated with ethanol concentrations of 1 wt %, 5 wt % and 20 wt % were equal to those obtained with the sample treated with ammonia solution without ethanol addition. In terms of total xylose produced, increasing ethanol concentrations resulted in increases in production of this sugar. When ethanol was used at 49 wt %, the digestibility of both glucan and xylan were significantly lower than those obtained with the sample treated with no ethanol addition. There could be a number of reasons for the observed adverse effects of 49 wt % ethanol on glucan and xylan digestibilities. Without being bound by theory, one possible cause was that very high ethanol concentration might have affected the physical structure of the corn stover in such a way that prevented efficient enzyme attacks.

Xylan Retention and Selectivity: Carbohydrates, such as glucan, xylan, galactan, arabinan, and mannan, are valuable feedstocks that can be converted to fuels and chemicals by chemical and biological methods. The objective of this study was to produce a carbohydrate-rich solid cake with low lignin contents. This goal was surprisingly achieved through the addition of ethanol to the ammonia solution to reduce the loss of xylan through solubilization. In the biological conversion of biomass, lignin has been known to exert a significant inhibitory effect on both enzyme and microbial activities (Kim, T. H., et al., Bioresource Technology, 90: 39-47 (2003); Chang, V. S., and M. T. Holtzapple, Appl. Biochem. Biotechnol., 84/86: 537 (2000); Converse, A. O., Substrate Factors Limiting Enzymatic Hydrolysis, Biotechnology in Agriculture, No. 9, CABI Publishing, UK, 93-106 (1996); Cowling, E. B., T. K. Kirk, Biotechnol. Bioeng Symp., 6: 95-123 (1976); Dunlap, C. E., et al., AIChE. Symp. Ser., 72 (158): 58

(1976)). Thus, a good pretreatment process is one that has high degree of lignin removal and low carbohydrate losses. To quantitatively examine these desired pretreatment characteristics we introduced two simple concepts as follows:

$$\text{Xylan retention[\%]} = (X_R/X_T) \times 100$$

where,
$X_R$: Xylan remaining
$X_T$: Total xylan content in the untreated biomass $$\text{Selectivity}[-] = m_{Lignin}/m_{Xylan}$$

where, $m_{Lignin}$ and $m_{Xylan}$ are the mass loss rate of lignin and xylan of the corn stover during the pretreatment.

It is clear from the above equation that higher lignin removal and lower xylan loss will result in higher selectivity. Selectivity was calculated for the ethanol concentrations used in this study and plotted in FIG. 6 together with xylan retention and xylan digestibility. The results surprisingly show that selectivity increased as ethanol concentrations increased up to 20 wt % in parallel with increases in xylan retention. Selectivity still increased after ethanol concentration was increased above 20 wt % but digestibility dropped. As discussed above, very high ethanol concentrations might have affected the structure of the treated corn stover and reduced the enzyme efficiency.

Figure 6:
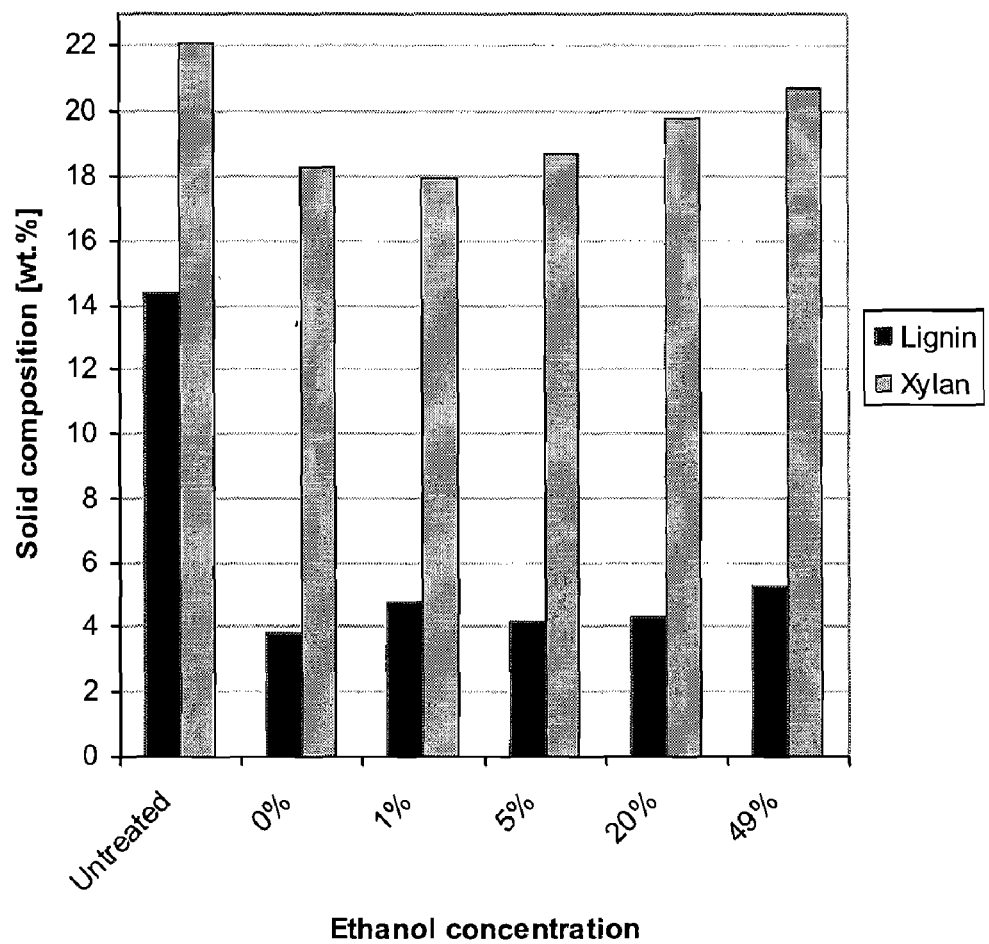
FIG. 6 shows compositional change in SEAA-treated corn stover with various ethanol concentrations.

Xylan retention at various ethanol concentrations are plotted in FIG. 6. The results surprisingly show the important role of ethanol in xylan retention. The highest ethanol concentration of 49 wt % resulted in an 11% improvement of xylan contents of the treated corn stover over the xylan contents of the sample treated with no ethanol addition. However, the digestibility of both glucan and xylan dropped significantly when ethanol concentration higher than 20 wt % was used. Thus, based on the experimental results obtained in this study, 20 wt % ethanol was the optimum concentration for the SEAA pretreatment of corn stover.

We have demonstrated that the addition of ethanol was effective for retention of hemicellulose during the SEAA treatment of corn stover. With optimum ethanol concentration at 20 wt %, the carbohydrate-rich solid sample obtained from SEAA treatment surprisingly contained 51.4% glucan, 26.7% xylan, and 6.2% lignin, which were almost 100% glucan retention, 89.6% xylan retention, and 70.1% lignin removal, respectively. The SEAA was proven to be an effective method to produce the carbohydrate-rich solid cake, which can be used for production of fuels and chemicals.

All of the references cited herein, including U.S. patents, are incorporated by reference in their entirety. Also incorporated by reference in their entirety are the following references: U.S. Pat. No. 4,644,060; Anderson, E., et al., J. Biol. Chem., 126 (1): 175-179 (1938); Doner, L. W., et al., U.S. Pat. No. 6,147,206; Gáspár, M., et al., Process Biochem., 42: 1135-1139 (2007); Gáspár, M., et al., Process Biochem., 40: 1183 1188 (2005); Horton, D., Eds.), Academic Press, New York, Vol. IIA, pp. 447-469 (1970); Sun, R. C., J. Tomkinson, Separation and Purification Technology, 24: 529 539 (2001); Sun, R. C., et al., Carbohydrate Polym., 44: 29-39 (2001); Whistler, R. L., and E. L. Richards, The Carbohydrates, Chemistry and Biochemistry (Pigman, W. and Horton, D., Eds.), Academic Press, New York, Vol. IIA, pp. 447-469 (1970).

Thus, in view of the above, the present invention concerns (in part) the following:

A method for improving the bioavailability of polysaccharides in lignocellulosic materials, comprising (or consisting essentially of or consisting of) reacting (contacting) for about 1 hour to about 72 hours said lignocellulosic materials with ammonia at a concentration of about 1 to about 30 wt % and ethanol at a concentration of about 1 wt % to about 49 wt % in a closed reactor vessel maintained at a temperature from about ambient temperature to about 170° C. (at a pressure fixed by thermodynamic equilibrium of the ammonia-water-ethanol system under the prescribed conditions) to form treated biomass and treated liquids.

A method for improving the bioavailability of polysaccharides in lignocellulosic materials, comprising (or consisting essentially of or consisting of) reacting (contacting) for about 1 hour to about 72 hours said lignocellulosic materials with ammonia at a concentration of about 1 to about 30 wt % and ethanol at a concentration of about 1 wt % to about 49 wt % at a temperature from about ambient temperature to about 170° C. to form treated biomass and treated liquids.

The above method, wherein said reacting is for about 8 hours to about 48 hours. The above method, wherein said reacting is for about 12 hours to about 24 hours. The above method, wherein said reacting is for about 20 hours to about 24 hours. The above method, wherein said reacting is for about 24 hours.

The above method, wherein said temperature is about 40° C. to about 120° C. The above method, wherein said temperature is about 50° C. to about 100° C. The above method, wherein said temperature is about 50° C. to about 70° C. The above method, wherein said temperature is about 60° C.

The above method, wherein said ammonia is at a concentration of about 5 wt % to about 25 wt %. The above method, wherein said ammonia is at a concentration of about 10 wt % to about 20 wt %. The above method, wherein said ammonia is at a concentration of about 14 wt % to about 16 wt %. The above method, wherein said ammonia is at a concentration of about 15 wt %.

The above method, wherein said ethanol is at a concentration of about 5 wt % to about 35 wt %. The above method, wherein said ethanol is at a concentration of about 10 wt % to about 25 wt %. The above method, wherein said ethanol is at a concentration of about 18 wt % to about 22 wt %. The above method, wherein said ethanol is at a concentration of about 20 wt %.

The above method, said method comprising (or consisting essentially of or consisting of) reacting (contacting) for about 1 hour to about 72 hours said lignocellulosic materials with ammonia at a concentration of about 1 to about 30 wt % and ethanol at a concentration of about 1 wt % to about 49 wt % in a closed reactor vessel maintained at a temperature from about ambient temperature to about 170° C.

The above method, further comprising separating said treated biomass from said treated liquids. The above method, further comprising washing said treated biomass. The above method, further comprising hydrolyzing said treated biomass with enzymes to produce fermentable sugars.

The above method, wherein said treated biomass contains more than about 83% of the xylan originally contained in said lignocellulosic materials. The above method, wherein said treated biomass contains more than about 90% of the xylan originally contained in said lignocellulosic materials. The above method, wherein said treated biomass contains about 94% of the xylan originally contained in said lignocellulosic materials. The above method, wherein said treated biomass contains more than about 94% of the xylan originally contained in said lignocellulosic materials.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Composition analysis of untreated corn stover.[1]

| Description | Composition [wt. % ± SD][2] |
|---|---|
| Glucan | 36.7 ± 0.2 |
| Xylan | 22.1 ± 0.2 |
| Galactan | 1.1 ± 0.0 |
| Arabinan | 3.8 ± 0.0 |
| Mannan | 0.3 ± 0.0 |
| Acid insoluble lignin | 14.4 ± 0.1 |
| Ash | 6.1 ± 0.1 |

[1]Data in the table are based on the oven-dried untreated biomass.
[2]Weight percent ± standard deviation (n = 2).

TABLE 2

The effect of ethanol concentrations on the compositions of corn stover in SEAA treatment[1]

| Ethanol concentration [wt. %] | Residual solids [%] | Lignin[2] [%] | Delignification [%] | Solid Glucan [%] | Solid Xylan [%] |
|---|---|---|---|---|---|
| Untreated | 100 | 14.4 | — | 36.1 ± 1.0 | 22.1 ± 0.0 |
| 0 | 65.1 ± 2.5 | 3.8 ± 0.5 | 73.6 ± 4.9 | 35.3 ± 1.0 | 18.3 ± 0.6 |
| 1 | 65.5 ± 1.1 | 4.8 ± 0.7 | 65.3 ± 6.9 | 35.1 ± 0.8 | 18.4 ± 0.2 |
| 5 | 66.6 ± 1.5 | 4.2 ± 0.3 | 70.8 ± 2.9 | 35.4 ± 1.4 | 18.9 ± 0.3 |
| 20 | 68.9 ± 2.4 | 4.3 ± 0.7 | 70.1 ± 6.9 | 35.4 ± 0.5 | 19.8 ± 0.6 |
| 49 | 72.5 ± 1.8 | 5.3 ± 0.4 | 63.2 ± 3.9 | 35.6 ± 0.6 | 20.7 ± 0.5 |

[1]Data in the table are based on the oven-dried untreated biomass (n = 2). Pretreatment conditions: 15 wt % of ammonia concentration, 60° C. of reaction temperature, 1:9 solid:liquid ratio (by weight), and 24 hour reaction time.
[2]Acid insoluble lignin.

We claim:

1. A method for improving the bioavailability of polysaccharides in lignocellulosic materials, said method comprising reacting for 1 hour to 72 hours said lignocellulosic materials with ammonia at a concentration of 14 to 30 wt % and ethanol at a concentration of 5 wt % to 49 wt % at a temperature from 40° C. to 70° C. to form treated biomass and treated liquids; wherein said treated biomass contains at least 85.5% of the xylan originally contained in said lignocellulosic materials.

2. The method according to claim 1, further comprising separating said treated biomass from said treated liquids.

3. The method according to claim 2, further comprising washing said treated biomass.

4. The method according to claim 2, further comprising hydrolyzing said treated biomass with enzymes to produce fermentable sugars.

5. The method according to claim 1, wherein said reacting is for 8 hours to 48 hours.

6. The method according to claim 1, wherein said reacting is for 12 hours to 24 hours.

7. The method according to claim 1, wherein said reacting is for 20 hours to 24 hours.

8. The method according to claim 1, wherein said reacting is for 24 hours.

9. The method according to claim 1, wherein said temperature is 50° C. to 70° C.

10. The method according to claim 1, wherein said temperature is 60° C.

11. The method according to claim 1, wherein said ammonia is at a concentration of 14 wt % to 16 wt %.

12. The method according to claim 1, wherein said ammonia is at a concentration of 15 wt %.

13. The method according to claim 1, wherein said ethanol is at a concentration of 5 wt % to 35 wt %.

14. The method according to claim 1, wherein said ethanol is at a concentration of 10 wt % to 25 wt %.

15. The method according to claim 1, wherein said ethanol is at a concentration of 18 wt % to 22 wt %.

16. The method according to claim 1, wherein said ethanol is at a concentration of 20 wt %.

17. The method according to claim 1, said method comprising reacting for 1 hour to 72 hours said lignocellulosic materials with ammonia at a concentration of 14 wt % to 30 wt % and ethanol at a concentration of 5 wt % to 49 wt % in a closed reactor vessel maintained at a temperature from 40° C. to 70° C.

18. The method according to claim 1, wherein said treated biomass contains 94% of the xylan originally contained in said lignocellulosic materials.

19. The method according to claim 1, wherein said treated biomass contains more than 94% of the xylan originally contained in said lignocellulosic materials.

20. The method according to claim 1, wherein said method consists of reacting for 1 hour to 72 hours said lignocellulosic materials with ammonia at a concentration of 14 wt % to 30 wt % and ethanol at a concentration of 5 wt % to 49 wt % in a temperature from 50° C. to 70° C. to form treated biomass and treated liquids; optionally separating said treated biomass from said treated liquids, and optionally washing said treated biomass, and optionally hydrolyzing said treated biomass with enzymes to produce fermentable sugars; wherein said treated biomass contains more than at least 85.5% of xylan originally contained in said lignocellulosic materials.

21. The method according to claim 1, wherein said treated biomass contains at least 89.6% of the xylan originally contained in said lignocellulosic materials.

22. The method according to claim 1, wherein said method comprises reacting for 1 hour to 72 hours said lignocellulosic materials with ammonia at a concentration of 14 to 16 wt % and ethanol at a concentration of 5 wt % to 49 wt % at a temperature from 50° C. to 70° C. to form treated biomass and treated liquids; wherein said treated biomass contains at least 85.5% of the xylan originally contained in said lignocellulosic materials.

23. The method according to claim 22, wherein said treated biomass contains at least 89.6% of the xylan originally contained in said lignocellulosic materials.

24. The method according to claim 1, wherein said ethanol is at a concentration of 20 wt % to 49 wt %.

* * * * *